(12) United States Patent
Carney et al.

(10) Patent No.: US 8,926,580 B2
(45) Date of Patent: Jan. 6, 2015

(54) ABSORBENT BELTED-ARTICLE WITH IMPROVED FRICTION BETWEEN THE ABSORBENT PAD AND THE BELT

(75) Inventors: Joshua Carney, Göteborg (SE); Kent Hermansson, Västra Frölunda (SE)

(73) Assignee: SCA Hygiene Products AB, Gothenburg (SE)

( * ) Notice: Subject to any disclaimer, the term of this patent is extended or adjusted under 35 U.S.C. 154(b) by 0 days.

(21) Appl. No.: 14/131,541

(22) PCT Filed: Jun. 29, 2012

(86) PCT No.: PCT/SE2012/050741
§ 371 (c)(1),
(2), (4) Date: Jan. 8, 2014

(87) PCT Pub. No.: WO2013/012376
PCT Pub. Date: Jan. 24, 2013

(65) Prior Publication Data
US 2014/0142534 A1    May 22, 2014

(30) Foreign Application Priority Data
Jul. 21, 2011    (CN) .......................... 2011 1 0208463

(51) Int. Cl.
*A61F 13/15* (2006.01)

(52) U.S. Cl.
USPC ............ 604/392; 604/386; 604/394; 604/396

(58) Field of Classification Search
USPC .................................. 604/386, 392, 394, 396
See application file for complete search history.

(56) References Cited

U.S. PATENT DOCUMENTS

| 4,964,860 A | 10/1990 | Gipson et al. |
| 5,906,604 A * | 5/1999 | Ronnberg et al. ............. 604/386 |

(Continued)

FOREIGN PATENT DOCUMENTS

| WO | WO 91/08725 A1 | 6/1991 |
| WO | WO 94/26222 A1 | 11/1994 |

(Continued)

OTHER PUBLICATIONS

International Search Report (PCT/ISA/210) mailed on Nov. 6, 2012, by the Swedish Patent as the International Searching Authority for International Application No. PCT/SE2012/050741.

(Continued)

*Primary Examiner* — Jacqueline F. Stephens
(74) *Attorney, Agent, or Firm* — Buchanan Ingersoll & Rooney PC

(57) ABSTRACT

An absorbent article includes an absorbent pad and a belt to which the pad is detachably attached and which is intended to be attached to a separate belt that is placed around the waist of the wearer to hold the pad when the article is being worn, wherein the absorbent pad exhibits a chassis including a liquid-permeable top sheet and a liquid-impermeable back sheet oriented away from the wearer and an absorbent core between the top sheet and the back sheet. The difference in kinetic coefficients of friction measured with ASTM D 1894-08 standard between the back sheet of the pad and the outwardly oriented surface of the belt is at maximum 0.5. The attachment between the belt and the pad will then not cease due to the movement of the article relative to the surroundings when the belted-article is being used, thereby preventing contamination and leakage caused by detachment.

14 Claims, 2 Drawing Sheets

(56) References Cited

U.S. PATENT DOCUMENTS

| | | |
|---|---|---|
| 2002/0042602 A1* | 4/2002 | Karlsson .................. 604/392 |
| 2004/0102749 A1 | 5/2004 | Olson et al. |
| 2005/0033257 A1 | 2/2005 | Miyoshi et al. |
| 2006/0247599 A1 | 11/2006 | Mullen et al. |
| 2008/0026178 A1 | 1/2008 | Stupperich et al. |
| 2008/0114326 A1 | 5/2008 | Roe et al. |

FOREIGN PATENT DOCUMENTS

| | | |
|---|---|---|
| WO | WO 94/26224 A1 | 11/1994 |
| WO | WO 94/26225 A1 | 11/1994 |
| WO | WO 99/21522 A1 | 5/1999 |
| WO | WO 01/30289 A1 | 5/2001 |
| WO | WO 01/43672 A2 | 6/2001 |

OTHER PUBLICATIONS

Written Opinion (PCT/ISA/237) mailed on Nov. 6, 2012, by the Swedish Patent Office as the International Searching Authority for International Application No. PCT/SE2012/050741.

International Preliminary Report on Patentability (PCT/IPEA/409) mailed on Jul. 16, 2013, by the Swedish Patent Office as the International Searching Authority for International Application No. PCT/SE2012/050741.

* cited by examiner

ABSORBENT BELTED-ARTICLE WITH IMPROVED FRICTION BETWEEN THE ABSORBENT PAD AND THE BELT

TECHNICAL FIELD

The present disclosure relates to an absorbent article comprising two separate components, i.e. an absorbent pad and a belt, which is also referred to as "belted-article". In particular, the present disclosure relates to an absorbent article with improved friction between the absorbent pad and the belt.

TECHNICAL BACKGROUND

The type of absorbent articles which consists of an absorbent pad and a belt to which the pad is detachably attached is well known in this field. Examples of this type of articles are disclosed in WO99/21522, WO94/26224, WO94/26222, WO94/26225 and U.S. Pat. No. 4,964,860.

When using a belted-article, the belt is first attached around the waist of the wearer and then the pad is attached to the belt. In particular, one end of the pad is attached to the belt on the front or back of the wearer and then the other end of the pad is pulled through between the legs of the wearer. Finally, the other end is attached to the belt on the back or front of the wearer.

The above belted-articles are often used for children or incontinent adults for absorption of bodily exudates, such as blood, urine, sweat and faeces. Therefore, the belted-articles will be in contact with the surroundings such as outer trousers or bedclothes. To avoid contamination or leakage, the connection between the absorbent pad and the belt is of importance. When the article moves relative to the surroundings, the attachment will be affected by the friction between the surroundings and the article as well as the materials of the pad and the belt. In particular, the attachment between the pad and the belt may be broken when the article moves relative to the surroundings.

WO 2001043672 A2 relates to an absorbent garment comprising a suspension sling (including an absorbent body) and a waist belt. The belt can be detachably attached to the suspension sling. It is also mentioned in connection to an alternative embodiment that the belt can be made from the same material as the back sheet of the suspension sling. However, WO 2001043672 A2 does not focus on friction and there is still a risk that the pad and the belt will be separated when the article interacts with the surroundings.

US 2004/0102749 A1 relates to absorbent articles comprising stretchable regions, wherein materials of the absorbent article which are in sliding contact with one another is prevented from sticking together. It is mentioned in US 2004/0102749 A1 that the problem is associated with disproportionately high difference in coefficients of the friction between said materials. Therefore, in US 2004/0102749 A1 the solution is achieved by minimizing the friction between said materials. It is stated that the coefficient of friction between the two materials in sliding contact with one another should not be greater than 0.4.

However, US 2004/0102749 A1 does not mention the friction between the article and the surroundings and the article is not a belted-article and can therefore not be attached to a separate belt.

US 2008/0114326 A1 relates to a disposable absorbent article configured to be placed on the body of a wearer to mimic swaddling characteristics. The disposable absorbent article may include a chassis having a tuck flap and two ears or side panels. US 2008/0114326 A1 shows that it is known to provide an absorbent article with ears made of the same material as the chassis. However, these ears are integral with the article, which is different from the belted-articles.

None of the articles in the prior art mentions the friction between the belted-article and the surroundings.

SUMMARY

As mentioned above, when using the above-mentioned belted-article, the belt is first attached around the waist of the wearer and the pad is then attached to the belt. When attaching the pad to the belt, one end of the pad is firstly attached to the belt on the back of the wearer or the front of the wearer.

The waist portion of the pad comprises hook elements in each corner. When attaching the first end of the pad to the belt, the hook areas are attached to the belt, i.e. the hook areas are pressed against the belt, but not pressed too hard against the body of the wearer.

Next the other free end (the end not yet attached to the belt of the pad) is pulled between the legs of the wearer and attached to the belt on the front of the wearer (or rear of the wearer).

The completed belted-article comprises the belt arranged around the waist of the wearer and the pad connected to the belt via the crotch.

During use the belted-article will be in contact with various surroundings such as trousers or bedclothes.

Movement between the belted-article and the surroundings may occur when a bedridden incontinent adult is moved in his/her bed when changing the incontinence article, when changing bedclothes or in any other way assisting the patient or adjusting his/her bed.

Often the patient is rolled from one side to his/her other side when changing incontinence article, which may cause relative movement between the article and the bedclothes.

One risky situation when there is a movement between the belted-article and surrounding material is when a pair of outer trousers is drawn up over the belted-article. If the belt then exhibits a much higher friction than the pad there is a risk that the belt attaches to the outer trousers but not the pad. The belt will follow the upward movement of the trousers and a disengagement of the pad from the belt may occur.

Another situation is when the outer trousers are drawn in the opposite way, i.e. when the trousers are removed from the wearer. If the coefficient of friction is much higher for the outer surface of the pad there is a risk that only the pad attach to the outer trousers with a possible result that the belt and the pad separate from each other.

When a person is leaning forward it is quite normal that the underpants slide relative the person (or relative the belted-article). If there is a big difference in friction between the belt and the pad there is a risk that the two components separate from each other.

There are of course many other situations when a movement between the belted-article and surrounding materials may occur, for example, when the wearer walks or runs, the attachment may be broken.

A problem to be solved by the present disclosure is to prevent the attachment between the belt and the pad to disengage under certain circumstances especially when the article is moved relative to the surroundings.

The inventors have found that the attachment (connection) is directly related to (i) the friction between the outer surface of the pad and the surroundings and (ii) the outwardly oriented surface of the belt and the surroundings.

Therefore, it is desired to provide a belted-article in which the friction between the outer surface of the pad and the surrounding as well as the friction between the outer surface of the belt and the surroundings are improved in order to prevent the pad and the belt from separating from each other when the article is used.

When a material slides against another material a reaction force occurs that is dependent on the coefficient of friction between the two materials ($F=\mu \times N$; where $\mu$ is the coefficient of friction and N is the normal force) which, of course, is known in the art.

Generally, the outer oriented material layer of the belt and the outer oriented material layer of the pad normally comprise different materials exhibiting different coefficient of friction.

When there is a relative movement between the belted-article and, for example, the bedclothes, a first reaction force is generated between the outwardly oriented surface of belt and the bedclothes and a second reaction force is generated between the outer surface of the pad and the bedclothes. The first reaction force is determined by the kinetic coefficient of friction between the outwardly oriented surface of the belt and the bedclothes and the second reaction force is determined by the kinetic coefficient of friction between the outer surface of the pad and the bedclothes.

If the difference in kinetic coefficients of friction is big, i.e. the reaction forces differ much, there is a risk that the attachment (connection) between the belt and the pad to be broken, or at least there is a risk of a reorientation of the attachment between the pad and the belt which may cause poor performance of the belted-article.

Although US 2004/0102749 A1 identifies friction as a source of problem, the problem is solved by preventing different materials of an absorbent article from sticking together. That is to say, US 2004/0102749 A1 does not focus on friction between different materials of an article in sliding contact with one another. Therefore the solution of US 2004/0102749 A1 is to minimize the friction between said materials.

Therefore, in view of the disadvantages above-mentioned, another problem to be solved by the present disclosure is to define the frictional surface characteristics of the belt and the pad relative each other.

An object of the present disclosure is to provide an absorbent belted-article with reduced difference in kinetic coefficients of friction between the outwardly oriented surface of the belt and the outer surface of the pad (i.e. the back sheet of the pad) in order to prevent the pad and the belt to become separated from one another during use.

The present disclosure provides an absorbent belted-article comprising an absorbent pad and a separate belt to which the pad is detachably attached and which is placed around the waist of the wearer to hold the pad when the article is being worn, wherein the absorbent pad exhibits a chassis comprising a liquid-permeable top sheet and a liquid-impermeable back sheet oriented away from the wearer (said back sheet thus forming an outer layer when the pad is being worn) and an absorbent core between the top sheet and the back sheet, and wherein the pad is detachably attached to the belt by an attaching arrangement, wherein the difference in kinetic coefficients of friction measured under ASTM D 1894-08 Standard between the back sheet of the pad and the outwardly oriented surface of the belt is maximum 0.5.

In a particular embodiment, the back sheet of the pad and the outwardly oriented surface of the belt are formed of different type of materials.

According to an embodiment, the kinetic coefficient of friction on the back sheet of the pad is between 0.2 and 0.5 and the kinetic coefficient of friction is between 0.2 and 0.8 for the outwardly oriented surface of the belt.

In particular, the difference in kinetic coefficients of friction between the back sheet of the pad and the outwardly oriented surface of the belt is 0.3 at maximum, such as 0.2 at maximum, and especially the kinetic coefficient of friction is approximately the same for the back sheet of the pad and the outwardly oriented surface of the belt.

In a specific embodiment, the attaching arrangement comprises hook materials provided on each corner of the pad and loop materials provided on the outwardly oriented surface of the belt.

Alternatively, the attaching arrangement comprises loop materials provided on each corner of the pad and hook materials provided on the outwardly oriented surface of the belt.

Also alternatively, the attaching arrangement comprises adhesive materials provided on each corner of the pad and landing zones provided on the outwardly oriented surface of the belt.

When the pad is provided with hook materials, the outwardly oriented layer of the belt may constitute a nonwoven layer, in particular a carded nonwoven layer.

In particular, the outer layer or back sheet of the pad may constitute a nonwoven layer, in particular a spun bond nonwoven layer.

In a further embodiment, the hook material may constitute moulded hooks, in particular, moulded hooks having a palm tree shape.

In the article of the present disclosure as described above, the kinetic coefficient of friction between the garment-facing side of the pad and the clothing is sufficiently close to the kinetic coefficient of friction between the outwardly oriented surface of the belt and the clothing, thereby ensuring that the belt will be moved about as much as the pad when the wearer is moving. Consequently, the belt will not be detached from the pad.

BRIEF DESCRIPTION OF THE DRAWINGS

The present disclosure will now be explained in more detail with reference to certain non-limiting embodiments and with reference to the accompanying drawings, in which.

DETAILED DESCRIPTION

Embodiments of the present disclosure will be described below with reference to the drawings.

The term "absorbent article" is to be understood as meaning an article selected from the group consisting of diapers, male or female incontinence guards, belted-diapers, etc. Such articles are used for the absorption of bodily exudates, such as blood, urine, sweat and faeces.

Figure 1:
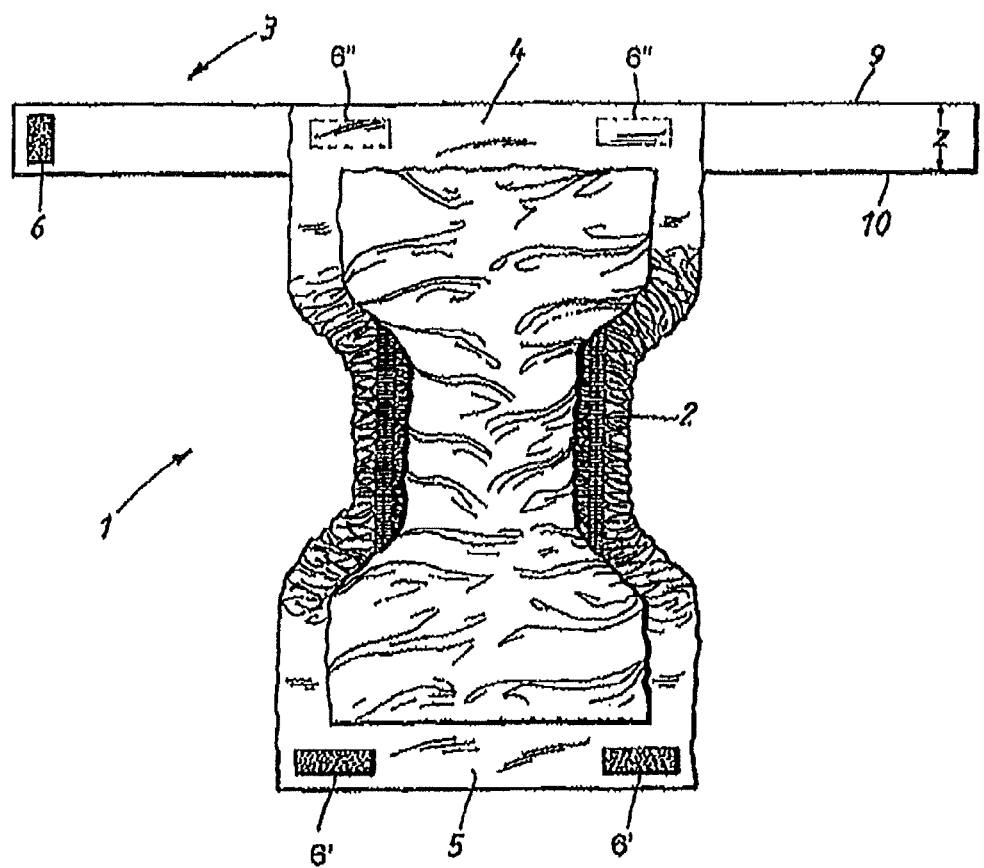
FIG. 1 is a plan view showing an absorbent article consisting of a belt and an absorbent pad attached thereto according to the present disclosure.

FIG. 1 shows an absorbent article 1 which consists of an absorbent pad 2 and a separate belt 3. The belt 3 is a continuous belt detachably attached to the two longitudinal ends 4, 5 of the absorbent pad 2 when wearing the article.

As shown in FIG. 1, at one end of the belt 3 there is provided a strip 6 of hook elements, which can either be secured to the outwardly oriented surface of the belt 3 or to a loop material arranged on the outwardly oriented surface on the belt. The belt 3 has an elongated rectangular shape comprising two laterally spaced edges 9 and 10 between which the strip 6 will be attached. Other shapes of the belt are also conceivable.

In particular, a non-woven material is used for either one or both sides of the belt 3, said non-woven material being of a type to which the hook elements of the strip 6 can be detachably attached.

Alternatively, the strip 6 on the belt can be an adhesive strip to be detachably attached to a landing zone on the outwardly oriented surface of the belt 3. Otherwise, the hook material can be exchanged with the loop material on the belt.

On each corner of the pad 2, there is a strip 6' or 6". FIG. 1 shows four strips, with two strips 6' arranged at the end 5 and the other two strips 6" arranged at the other end 4. These strips 6', 6" are used to be detachably attached to the outwardly oriented surface of the belt 3. In particular, these strips 6', 6" are formed of the same material(s) as the strip 6 on the belt 3, such as hook materials. Accordingly the surface of the belt comprises loop material.

In an alternative embodiment, the hook material constitutes moulded hooks. Especially, the hook material constitutes moulded hooks having a palm tree shape.

Alternatively, the hook material on the pad and the loop material on the belt can be switched. In a further alternative, the hook material may be displaced with adhesive material to be attached to the landing zones on the belt.

The absorbent pad shown in FIG. 1 comprises a chassis having a liquid-permeable top sheet, a liquid-impermeable back sheet and an absorbent core located there between.

The top sheet of the absorbent pad is the layer which lies in contact with the wearer's body when the pad is in use. As such, it should be soft, non-irritating and comfortable against the skin, and bodily fluid should be able to pass through it without hindrance.

The back sheet of the absorbent pad is the layer which lies furthest from the wearer's body when the pad is in use. To protect the wearer's garments from soiling, it should be liquid-impermeable, but is desirably gas-permeable (i.e. breathable) to allow air and vapour to pass in and out of the article so that the warm, damp conditions which can arise in the pad are reduced.

The absorbent core of the absorbent pad acts to receive and contain liquid and other bodily exudates. As such, it typically comprises absorbent material.

The absorbent core may comprise one or more layers which are designed to improve the handling of bodily waste.

After the article is put on the wearer, the outer surface of the pad, i.e. the back sheet, and the outwardly oriented surface of the belt will be in contact with the surroundings such as trousers and bedclothes.

As mentioned above, the friction between the article and the surroundings, that is the friction between the back sheet of the pad and the surroundings and the friction between the outwardly oriented surface of the belt and the surroundings will significantly affect the attachment between the belt and the pad.

In order to prevent the pad and the belt separating from each other when the wearer moves, the friction between the back sheet, the outwardly oriented surface of the belt and the surroundings are thus important and will be described in detail with reference to FIGS. 2-3.

Figure 2:
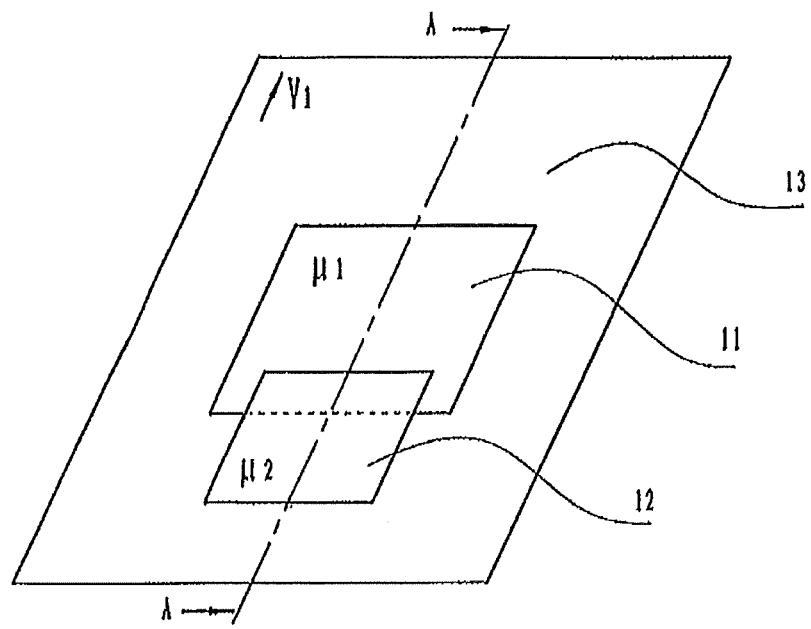
FIG. 2 is a plan view showing the principle of the friction between the outer surface of the pad and the surroundings as well as between the outer surface of the pad and the surroundings.

FIG. 2 is a theoretic schematic view showing the friction relations between the outwardly oriented surface of the belt, the back sheet of the pad, and the surroundings.

Figure 3:
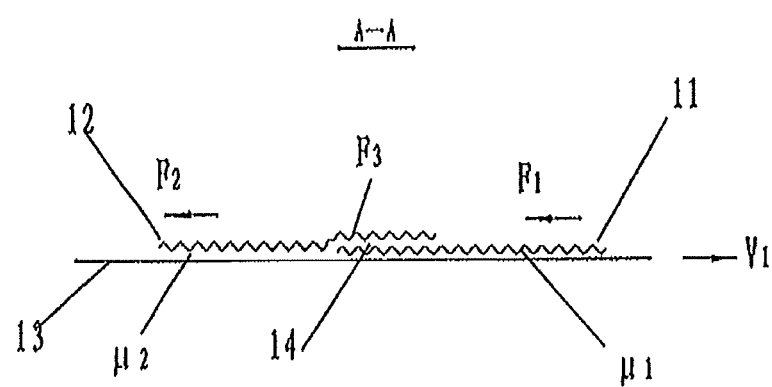
FIG. 3 is a section view taken along the line A-A in FIG. 2.

FIG. 3 is a section view taken along the line A-A in FIG. 2.

The theory underlying the present disclosure can be understood from the sliding of material 11 and material 12 on the outer material 13 as shown in FIGS. 2-3.

In FIGS. 2-3, "outer surface" assigned with reference sign 13 represents a surrounding material sliding against the belted-article when or after the article is put on. Material assigned with reference sign 11 represents either the belt material or the pad material and material assigned with reference 12 represents the other of the belt or the pad material.

When the outer material 13 is sliding over material 11 and material 12 at speed $V_1$, the reaction force $F_1$ acting on material 11 and reaction force $F_2$ acting on material 12 are generated.

The following description is described, for example, in connection to the bedridden patient.

According to the known principle of friction, $F_1=\mu_1 \times N$ (N is the external force, i.e. for example the force caused by the weight of the wearer), and $F_2=\mu_2 \times N$ The force acting on the attachment between the two materials (the belt material and the pad material) constituting outer surfaces of the belted-article is $F_3$ and $$F_3=F_1-F_2=N\times(\mu_1-\mu_2)$$

$\mu_1$ and $\mu_2$ are the kinetic coefficients for the back sheet of the pad and the outwardly oriented surface of the belt, respectively.

The magnitude of $F_3$ directly affects the attachment between the pad and the belt. If this force $F_3$ is larger than the force required for separating the pad from the belt, the attachment will cease. It is obvious that the lower force $F_3$ is advantageous.

According to the above equation, the force acting on the attachment between the outwardly oriented surfaces of the belt and the pad is related to the difference in the kinetic coefficient of friction. That is to say, the lower the difference in kinetic coefficients of friction between the belt and the pad is, the lower is the force acting on the attachment between the belt and the pad. If the kinetic coefficient of friction is the same, then the force $F_3$ is zero, which is favorable since the attachment between the belt and the pad then not is affected by the movement of the article relative to the surroundings.

While testing various belt materials and back sheet materials, the inventors found that:

In particular, the outwardly oriented material of the belt has a kinetic coefficient of friction between 0.2 and 0.8. In particular, the outer surface of the back sheet has a kinetic coefficient of friction between 0.2 and 0.5.

The maximum difference in kinetic coefficient of friction said materials is equal to or less than 0.5.

This means that the maximum force acting on the attachment between the belt and the pad is $F_3=N\times(\mu_1-\mu_2)=N\times0.5$.

For better understanding of the effect of this force caused by friction, some approximate forces based on the bedridden incontinent patient are listed below. Under the condition that the difference in kinetic coefficients of friction between the belt and the pad is 0.5, $F_3$ is:

250 N when N=500 N (approx full weight of a person with a weight of 50 Kg)

375 N when N=750 N (approx full weight of a person with a weight of 75 Kg)

500 N when N=1000 N (approx full weight of a person with a weight of 100 Kg)

625 N when N =-1250 N (approx full weight of a person with a weight of 125 Kg)

750 N when N=1500 N (approx full weight of a person with a weight of 150 Kg)

That is to say, the force acting on the attachment between the pad and the belt is within an acceptable range even if the bedridden patient is very heavy.

The inventors have measured various belt materials and pad materials and the following kinetic coefficients of friction have been obtained.

| Material<br>NW = Nonwoven<br>SMS = Spunbond/Meltblown/Spunbond<br>SMMS = Spunbond/Meltblown/Meltblown/Spunbond | Supplier | Use | Average kinetic coefficient of friction (ASTM D 1894-08) |
| --- | --- | --- | --- |
| Spun bond 16 gsm | From Union, Italy | Back sheet | 0.31 |
| SMS NW 17 gsm | Freudenberg, Germany | Back sheet | 0.24 |
| Spun bond 16 gsm | Freudenberg, Germany | Back sheet | 0.27 |
| Spun bond TS 13 gsm SMMS | DeaMyung chemical co, ltd Korea | Back sheet | 0.41 |
| Spun bond 50 gsm | Golden Phoenix, Fiberweb, Taiwan | Belt | 0.15 (outside the scope) |
| Spun Bond 50 gsm | PGI, Morsville USA | Belt | 0.24 |
| Lamitex 80 Carded NW | Fiberweb Tenotex S.p.a. Italy | Belt | 0.71 |

The inventors also made a series of tests on the difference in kinetic coefficients of friction and the attachment. The tests demonstrate that the kinetic coefficient of friction in the abovementioned selected ranges can achieve the desired effects, i.e. the belt is difficult to separate from the pad when the article is moved relative the surroundings. All the tests show that when the difference in kinetic coefficients of friction between the outwardly oriented surfaces of the belt and the pad is smaller than 0.5, the force acting on the attachment between the belt and the pad is minimized even if the bedridden patient is heavy, thereby the attachment between the belt and the pad is not easy detach with the movement of the article relative to the surroundings when the article is used.

After testing, the inventors found that a suitable kinetic coefficient of friction for the outwardly oriented surface of belt particularly is between 0.2 and 0.8. Moreover, it was found that a particularly suitable kinetic coefficient of friction for the back sheet of the pad is between 0.2 and 0.5.

Under the proviso that the requirement of kinetic coefficient of friction is fulfilled, the belt and the pad may be made of different materials with similar kinetic coefficient of friction.

Alternatively, the belt and the pad may be formed of the same material.

In a specific embodiment, the outwardly oriented layer of the belt constitutes a nonwoven layer. Especially, the outwardly oriented layer of the belt constitutes a carded nonwoven layer.

In a further specific embodiment, the outer layer or back sheet of the pad constitutes a nonwoven layer, in particular the outer layer of the pad constitutes a spun bond nonwoven layer.

Although the embodiments of the present disclosure have been described above, the present disclosure is not limited to the above embodiments, but various changes and modification may be made therein within the scope of the technical concept described in the scope of the claims.

The invention claimed is:

1. An absorbent belted-article comprising an absorbent pad and a separate belt to which the absorbent pad is detachably attached and which is to be placed around the waist of a wearer to hold the absorbent pad when the belted-article is being worn, wherein the absorbent pad includes a chassis which comprises a liquid-permeable top sheet and a liquid-impermeable back sheet oriented away from the wearer and an absorbent core between the top sheet and the back sheet, and wherein the absorbent pad is detachably attached to the belt by an attaching arrangement, wherein the difference in kinetic coefficients of friction between the back sheet of the absorbent pad and an outwardly oriented surface of the belt is 0.5 at maximum, wherein the kinetic coefficient of friction of the back sheet of the absorbent pad and a surrounding material and the kinetic coefficient of friction of the outwardly oriented surface of the belt and said surrounding material, respectively, are measured with ASTM D 1894-08 standard, and the back sheet of the absorbent pad and the outwardly oriented surface of the belt are formed of different type of materials.

2. The absorbent belted-article according to claim 1, wherein the kinetic coefficient of friction of the back sheet of the absorbent pad and the surrounding material is between 0.2 and 0.5 and the kinetic coefficient of friction on the outwardly oriented surface of the belt and said surrounding material is between 0.2 and 0.8.

3. The absorbent belted-article according to claim 1, wherein the difference in kinetic coefficients of friction between the back sheet of the absorbent pad and the outwardly oriented surface of the belt is 0.3 at maximum.

4. The absorbent belted-article according to claim 1, wherein the difference in kinetic coefficients of friction between the back sheet of the absorbent pad and the outwardly oriented surface of the belt is 0.2 at maximum.

5. The absorbent belted-article according to claim 1, wherein the kinetic coefficient of friction is approximately the same for the back sheet of the absorbent pad and the surrounding material and for the outwardly oriented surface of the belt and the surrounding material.

6. The absorbent belted-article according to claim 1, wherein the attaching arrangement comprises hook materials provided on each corner of the absorbent pad and loop materials provided on the outwardly oriented surface of the belt.

7. The absorbent belted-article according to claim 6, wherein the attaching arrangement comprises loop materials provided on each corner of the absorbent pad and hook materials provided on the outwardly oriented surface of the belt.

8. The absorbent belted-article according to claim 6, wherein the outwardly oriented surface of the belt constitutes a nonwoven layer.

9. The absorbent belted-article according to claim 8, wherein the outwardly oriented surface of the belt constitutes a carded nonwoven layer.

10. The absorbent belted-article according to claim 6, wherein the hook material constitutes moulded hooks.

11. The absorbent belted-article according to claim 6, wherein the hook material constitutes moulded hooks having a palm tree shape.

12. The absorbent belted-article according to claim 1, wherein the attaching arrangement comprises adhesive materials provided on each corner of the absorbent pad and landing zones provided on the outwardly oriented surface of the belt.

13. The absorbent belted-article according to claim 1, wherein the back sheet of the absorbent pad constitutes a nonwoven layer.

14. The absorbent belted-article according to claim 13, wherein the back sheet of the absorbent pad constitutes a spun bond nonwoven layer.

* * * * *